US009897546B2

(12) United States Patent
Courtney (10) Patent No.: US 9,897,546 B2
(45) Date of Patent: Feb. 20, 2018

(54) DEVICE FOR OPTICALLY MEASURING FLUORESCENCE OF NUCLEIC ACIDS IN TEST SAMPLES AND USE OF THE DEVICE

(71) Applicant: Hain Lifescience GmbH, Nehren (DE)

(72) Inventor: James Courtney, Kent (GB)

(73) Assignee: Hain Lifescience GmbH, Nehren (DE)

( * ) Notice: Subject to any disclaimer, the term of this patent is extended or adjusted under 35 U.S.C. 154(b) by 0 days.

(21) Appl. No.: 14/361,826

(22) PCT Filed: Dec. 4, 2012

(86) PCT No.: PCT/EP2012/074298
§ 371 (c)(1),
(2) Date: May 30, 2014

(87) PCT Pub. No.: WO2013/087446
PCT Pub. Date: Jun. 20, 2013

(65) Prior Publication Data
US 2015/0233828 A1 Aug. 20, 2015

(30) Foreign Application Priority Data
Dec. 15, 2011 (EP) ..................................... 11193698

(51) Int. Cl.
*G01N 21/64* (2006.01)
*G01N 21/31* (2006.01)
*G01J 3/44* (2006.01)

(52) U.S. Cl.
CPC ......... *G01N 21/6486* (2013.01); *G01N 21/31* (2013.01); *G01N 21/6454* (2013.01); *G01N 21/64* (2013.01)

(58) Field of Classification Search
CPC ............... G01N 21/6486; G01N 21/64; G01N 21/6454; G01N 21/6452; G01N 21/31; G01J 3/4406

(Continued)

(56) References Cited

U.S. PATENT DOCUMENTS 5,525,300 A * 6/1996 Danssaert ................. B01L 7/52
422/552
5,736,106 A * 4/1998 Ishiguro .................... B01L 7/52
165/133

(Continued)

FOREIGN PATENT DOCUMENTS

JP          2011-234639    * 11/2011    .............. C12M 1/00
WO    WO 2008/116186 A1    9/2008
WO    WO 2010/118541 A1    10/2010

OTHER PUBLICATIONS

Labcon catalog, 2010, http://repfon.com/docs/pdf/Labcon2010webcatalog.pdf, pp. 1-82.*

(Continued)

*Primary Examiner* — David Porta
*Assistant Examiner* — Blake Riddick
(74) *Attorney, Agent, or Firm* — Curatolo Sidoti Co., LPA; Joseph G. Curatolo; Vincent A. Cortese (57) ABSTRACT

The invention relates to a device (12; 72) for optically measuring fluorescence of nucleic acids in test samples (14). The device (12; 72) comprises a plurality of sample wells (32) each for receiving an upright sample tube (16) made of a transparent material, having a side wall (20) and a bottom end (22) and containing one of the test samples (14) together with at least one fluorescent dye, at least one excitation light source (24; 74, 76, 78, 80) disposed in the vicinity of each sample well (32) for directing an excitation light beam through the side wall (20) of the sample tube (16) into the test sample (14) for exciting the dye, and an optical fluorescence detector (28) disposed underneath the bottom end (22) of each sample tube (16) for capturing fluorescence emitted from the dye in the test sample (14) upon excitation.

13 Claims, 4 Drawing Sheets (58) Field of Classification Search
USPC .................. 250/458.1, 459.1, 461.2
See application file for complete search history.

(56) References Cited

U.S. PATENT DOCUMENTS

| | | | |
|---|---|---|---|
| 6,036,920 A * | 3/2000 | Pantoliano | B01L 7/00 250/458.1 |
| 6,337,435 B1 * | 1/2002 | Chu | B01L 7/52 136/203 |
| 6,515,743 B1 * | 2/2003 | Hayashi et al. | 356/317 |
| 6,582,962 B1 * | 6/2003 | Richards et al. | 436/46 |
| 7,466,908 B1 | 12/2008 | Porat et al. | |
| 2002/0044885 A1 * | 4/2002 | Hearst et al. | 422/22 |
| 2004/0224317 A1 | 11/2004 | Kordunsky et al. | |
| 2006/0024831 A1 * | 2/2006 | Kao | B01L 3/50851 356/243.1 |
| 2006/0152727 A1 * | 7/2006 | Bickmore, Jr. | G01N 21/6452 356/417 |
| 2007/0021929 A1 * | 1/2007 | Lemmo et al. | 702/22 |
| 2007/0039866 A1 * | 2/2007 | Schroeder | B01L 3/502715 210/265 |
| 2007/0059754 A1 | 3/2007 | Kordunsky et al. | |
| 2007/0099208 A1 * | 5/2007 | Drmanac et al. | 435/6 |
| 2007/0172941 A1 | 7/2007 | Porat et al. | |
| 2008/0031774 A1 * | 2/2008 | Magnant et al. | 422/63 |
| 2008/0032416 A1 * | 2/2008 | Park et al. | 436/172 |
| 2008/0057542 A1 * | 3/2008 | Roberts et al. | 435/91.2 |
| 2008/0057544 A1 * | 3/2008 | Lem et al. | 435/91.2 |
| 2008/0096193 A1 * | 4/2008 | Bupp et al. | 435/6 |
| 2008/0108072 A1 * | 5/2008 | Chicoine et al. | 435/6 |
| 2008/0166727 A1 * | 7/2008 | Esfandyarpour et al. | 435/6 |
| 2008/0176232 A1 * | 7/2008 | Lee | B01L 7/52 435/6.11 |
| 2008/0229849 A1 * | 9/2008 | Doebler et al. | 73/864.91 |
| 2008/0268434 A1 * | 10/2008 | Nurmi | B01L 7/5255 435/6.18 |
| 2009/0221059 A1 * | 9/2009 | Williams | B01L 3/5027 435/287.2 |
| 2010/0221704 A1 * | 9/2010 | Hanafusa et al. | 435/6 |
| 2010/0227386 A1 * | 9/2010 | Neuzil et al. | 435/288.7 |
| 2011/0152128 A1 * | 6/2011 | Herrmann et al. | 506/40 |
| 2011/0160073 A1 | 6/2011 | Kordunsky et al. | |
| 2011/0236903 A1 * | 9/2011 | McClelland et al. | 435/6.14 |
| 2012/0171756 A1 | 7/2012 | Doebler, II et al. | |
| 2013/0078712 A1 * | 3/2013 | Sano | G01N 35/025 435/289.1 |
| 2014/0203173 A1 * | 7/2014 | Krufka | G01J 3/10 250/214 R |
| 2014/0255945 A1 * | 9/2014 | Hendrikx | 435/6.12 |

OTHER PUBLICATIONS

PCT/EP2012/074298—International Search Report, dated Apr. 23, 2013.
PCT/EP2012/074298—International Written Opinion, dated Apr. 23, 2013.
PCT/EP2012/074298—International Preliminary Report on Patentability, dated Jan. 9, 2014.

* cited by examiner

DEVICE FOR OPTICALLY MEASURING FLUORESCENCE OF NUCLEIC ACIDS IN TEST SAMPLES AND USE OF THE DEVICE

CROSS REFERENCE TO RELATED APPLICATIONS

This application is a national stage application of International Application No. PCT/EP2012/074298, filed 4 Dec. 2012, which claims priority from European Patent Application No. 11193698.5, filed 15 Dec. 2011, from which applications priority is claimed, and which are incorporated herein by reference.

This invention relates to fluorescence measurement of test samples. Specifically, the present invention is directed to a device for optically measuring fluorescence of test samples according to the preamble of claim 1. More specifically the invention relates to the fluorescence measurement of nucleic acids in test samples.

STATE OF THE ART

Standard PCR (Polymerase Chain Reaction) is well known in the art and is used to amplify a targeted sequence of DNA, however might be used for amplifying RNA as well. With standard PCR the amplified DNA sequence is detected at the end of the chain reaction using Agarose gels. As an alternative various fluorescent dye-based methods are known, where the detection and/or quantification of the amplified DNA sequence in a test sample can be performed by optical fluorescence measurement during the reaction in real time. In other words the amplified DNA sequence in the test sample is measured at each PCR cycle. This form of PCR is known as Quantitative PCR (QPCR) or Real-time PCR. Examples of fluorescent dyes which are used with these methods are Sybr Green, EvaGreen or FRET-type fluorophore-containing DNA probes, such as TaqMan. These dyes typically intercalate or bind only with double-stranded DNA (dsDNA), i.e. the product of the PCR-cycle, which causes the fluorescence of the dye. An increase in DNA product during the reaction therefore leads to an increase in fluorescence intensity at each cycle. This increase can be measured with a fluorescence detector, thus allowing DNA concentrations to be quantified by comparison with a standard sample dilution. The obtained measurement data can be plotted against the number of cycles on a logarithmic scale and can be analyzed by computer software for relative or absolute quantification of amplified DNA. Real-time PCR can also be applied to the detection and quantification of DNA in samples to determine the presence and abundance of a particular DNA sequence in these samples.

Similar fluorescent dye-based methods can be applied in the Melting Curve Analysis (MCA) which is an assessment of the dissociation-characteristics of double-stranded DNA during heating, i.e. a measurement of the dissociation of amplified DNA against temperature.

Devices for performing PCR are known as thermal cyclers and devices for performing optical fluorescence measurement of DNA in test samples during Real Time/Qualitative PCR or during Melting Curve Analysis are often called "optical-type" thermal cyclers.

These "optical type" thermal cyclers comprise means for alternately heating and cooling the test samples during the cycles of the Real Time/Qualitative PCR or for heating the test samples during the Melting Curve Analysis respectively, in combination with at least one excitation light source for exciting the fluorescent dye in the test samples and at least one optical fluorescence detector for measuring the fluorescence emitted by the dye upon excitation. The means for heating and cooling the test samples may advantageously comprise Peltier devices for facilitating rapid temperature changes of the test samples. As with standard thermal cyclers, heated lids are used to minimize sample evaporation during the thermal cycling process.

In currently available optical-type thermal cyclers for use with standard plastic sample tubes, e.g. standard plastic micro-centrifuge sample tubes customarily used for DNA analysis, both the excitation light sources and the optical fluorescence detectors are disposed above the wells for the sample tubes in a hinged lid of the device. In these cyclers the excitation of the dye and the detection of the fluorescence are performed through the open top of the sample tubes. However when using a heated lid the lid has to be perforated or partly transparent for passing the excitation light and the fluorescence which adds to the complexity of the device. Furthermore this configuration suffers from a so-called variation in optical alignment, i.e. positional deviations of the excitation light sources and the optical fluorescence detectors with respect to the sample wells or sample tubes, which may be caused for example by tolerances of the movable lid.

Variations in optical alignment are typical in thermal cyclers having moving components for positioning the excitation light source or the optical detector system or both above the sample wells containing the open sample tubes. Such a thermal cycler is for example disclosed in WO2010/118541 A1 where optical units comprising an excitation light source and a detector are rotated with respect to sample chambers each containing a test sample. Variations in optical alignment are also typical in thermal cyclers having a motorized movable tray for moving the sample tubes into and out of a treatment and measurement position.

Some of the prior art optical-type thermal cyclers require the placement of the test samples in dedicated, custom-made sample chambers and do not allow for the measurement of test samples in customary sample tubes, e.g. standard plastic micro-centrifuge sample tubes which are used for DNA analysis.

U.S. Pat. No. 6,515,743 B1 discloses a scanner-type device according to the preamble of claim 1 for the measurement of a fluorescent reaction product by an enzyme reaction. The device comprises a plurality of sample wells each for receiving an upright sample tube made of a transparent material and containing a test sample. The sample wells are disposed on a circular arc having a drive unit for rotating the arc and successively moving the sample wells into the vicinity of a single excitation light source. The excitation light source directs an excitation light beam through the side wall of one of the sample tubes. The device further comprises at least one optical fluorescence detector for capturing fluorescence emitted from one of the test samples through the bottom of the sample tube. An optical path between the bottom of the sample tube and the fluorescence detector comprises a light guide having an emission end placed on the rotation centre axis of the circular arc.

DETAILED DESCRIPTION OF THE INVENTION

One object of the invention is to provide a device and a method for optically measuring fluorescence of nucleic acids in test samples which can avoid any variations in optical alignment. Another object of the invention is to provide a device and method for optically measuring fluorescence of nucleic acids in test samples which allows the use of customary sample tubes, in particular standard micro-centrifuge tubes. It is a further object of the invention to provide a device for optically measuring fluorescence of nucleic acids in test samples such that neither excitation or detection of fluorescence is performed from above the test sample, thereby facilitating easy access to the sample wells, removal of the requirement for perforations or transparent windows in the lid for optical transmission, and the potential for utilizing other means than a heated lid to prevent sample evaporation.

In order to achieve these objects the present invention provides a device for optically measuring fluorescence of nucleic acids, preferably DNA, in test samples according to claim 1. Furthermore the present invention provides the use of the device for Real-Time/Qualitative PCR and/or for Melting Curve Analysis.

With the device according to the invention it is possible to locate the excitation light source, the sample well and the fluorescence detector in a unitary part of the device so that any potential movement relative to each other and therefore any variations of optical alignment can be avoided. Therefore a robust and consistent optical alignment is fully assured.

Surprisingly it is possible with the device according to the invention to use standard or customary sample tubes, in particular standard micro-centrifuge tubes, which are normally made from transparent or translucent polyethylene. Transparent polyethylene has a light transmittance or clarity of less than 90%, mostly around 80%, and is therefore not considered an "optical grade" material such as deemed necessary for optical fluorescence measurements.

In addition the device according to the invention can facilitate access to the sample tubes in the sample wells by means of a lid, hinged or otherwise, which if required can be in the form of a standard metal plate as there is no need for perforations or transparent windows in the lid. Advantageously the lid applies a pressure to the caps of the sample tubes in order to keep the caps closed and the sample tubes in good thermal contact with the walls of the sample wells during thermal cycling. Preferably the lid may be provided with a cheap and simple resistance heater which can be used to heat the air in the top of the sample tubes thereby minimizing sample evaporation and preventing the sample from condensing in the top or cap of the tube. When it is preferred to leave the sample tubes open during thermal cycling an oil or wax overlay might be added on top of the samples in the sample tubes to prevent evaporation. As there is no need for light transmission through the oil or wax overlay the latter may be opaque or temporarily opaque, e.g. when it solidifies during cooling cycles.

As compared with optical thermal cyclers with moving parts, like the one in WO2010/118541 A1, there is no measurement time delay associated with mechanically moving the parts with respect to each other.

In the context of the present invention the term "sample tube" is meant to refer to an elongated, generally tubular container or vial used for testing DNA- or RNA-samples. The sample tubes need not be cylindrical but may be slightly conical along their entire length or along a portion thereof.

As was already mentioned above, surprisingly the optical configuration of the device according to the invention allows for the use of standard sample tubes, in particular standard micro-centrifuge tubes. However even though there is no need to manufacture the sample tubes from an optical grade material, it may be of advantage to use a clear transparent material with a light transmittance of more than 90% for the manufacture of the sample tubes in order to enhance the amount of fluorescent light impinging onto the fluorescence detector at a given time, i.e. the yield of the detector. Due to the fact that the sample tubes are consumables they are advantageously made of plastic material. Preferably they are injection molded from a thermoplastic material. A preferred thermoplastic material with a high transmittance of clarity for the manufacture of the sample tubes for the device according to the invention may be Polyethyleneterephthalate (PET) due to its excellent light transmittance and its relatively low costs.

Most preferably, but not necessarily, the sample tubes are micro-centrifuge tubes with a standard shape which are suited for the device according to the present invention. However in order to enhance the transmittance of the bottom wall at the closed bottom ends of the sample tubes which face the fluorescence detectors the sample tubes can be provided with a flat bottom end instead of the convexly rounded bottom end of standard micro-centrifuge tubes. The sample tubes have a volume which is preferably smaller than 1 ml and may be either 0.2 or 0.5 ml.

According to a further preferred embodiment of the invention the cross sectional shape of the sample wells for receiving the upright sample tubes is adapted to the cross sectional shape of the sample tubes. Due to this it is possible on one hand to prevent measurement variations from test to test or sample to sample because the sample tubes are firmly maintained in a definite position with respect to the excitation light source and the fluorescence detector, preferably in a position where the sample tubes are centered within the sample wells so that the axis of the sample tubes are each in alignment with the fluorescence detectors located underneath their bottom ends. The centering of the sample tubes within the sample wells also contributes to a maximum yield of the fluorescence detectors. On the other hand the heat transfer from the walls of the sample wells to the sample tubes can be enhanced in order to be able to more rapidly heat or cool the test samples in the sample tubes.

Advantageously each excitation light source is a LED which emits light of a specific wavelength spectrum including a wavelength adapted to excite a specific fluorescent dye added to the DNA in the sample tube. Suitable LEDs are available at a relatively low price, do not comprise any moving parts and have a long lifetime. In addition they will occupy only limited space in the thermal cycler.

With one or more LEDs per sample well each test sample can be easily and simply calibrated with respect to fluorescence, i.e. each well can be calibrated individually. In addition one or more LEDs per sample well will ensure constantly a high light intensity per well and will avoid well to well illumination variations.

Preferably each optical fluorescence detector comprises a single photodiode. Photodiodes will measure the fluorescence emitted from the dye with high accuracy, have a long lifetime with high reliability and are available at relatively low costs. However instead of a photodiode each fluorescence detector might also comprise a Charge Coupled Device (CCD) for measuring the amount of fluorescent light impinging onto a detector surface of the detector. With a dedicated photodiode per sample well analysis will be full and consistent and not susceptible to cross-talk interference.

For preventing measurement variations from well to well the lengths of the optical paths from each excitation light source to the associated fluorescence detector are the same for all sample wells, i.e. the radial length of a first optical path from each excitation light source to the axis of the sample well or sample tube and the axial length of a second optical path from the intersection of the first optical path with the axis of the sample well or sample tube to the detector surface of the fluorescence detector are identical for all the sample wells.

In order to block any light in the wavelength spectrum of the excitation light source which does not contribute to the excitation of the specific fluorescent dye or dyes added to the sample in the sample tube according to a further preferred embodiment of the invention it is contemplated to dispose an optical excitation filter in the path of the excitation light beam between the excitation light source and the side wall of the associated sample tube, the excitation filter being adapted to transmit only light of the specific wavelength or wavelengths suited for exciting the specific fluorescent dye or dyes added to the sample. Furthermore an optical emission light filter is preferably disposed between the bottom end of the sample tube and the optical fluorescence detector, the emission filter being adapted to transmit only the fluorescent light emitted from the dye or dyes. Both filters will help to prevent any stray light from impinging onto the detector.

The device of the present invention may be used with advantage for either Melting Curve Analysis and/or for Real-Time/Qualitative PCR.

If the device according to the invention is used for Melting Curve Analysis then each sample well is preferably provided with a single excitation light source. Preferably the excitation light source is a single LED disposed in a radial bore in a wall of each sample well such that the mouth of the bore is facing the side wall of the sample tube inserted into the sample well in order to direct the excitation light beam along the bore and through the side wall of the sample tube into the test sample for exciting the fluorescent dye therein. The excitation light filter, if any, is preferably located at the mouth of the bore in proximity to the side wall of the sample tube.

In the device for performing Melting Curve Analysis any fluorescence emitted by the fluorescent dye in the sample is detected by means of a single photodiode of the fluorescence detector that is positioned directly underneath the sample tube, conveniently in a distance sufficient for mounting an optical emission filter between the bottom end of the sample tube and a detector surface of the detector. Preferably the optical emission filter is a single narrow band-pass filter which is designed to transmit the wavelengths particular to the fluorescence emission spectrum of the dye in the sample tubes and to block all other wavelengths.

On the other hand, if the device according to the invention is used for Real-Time/Qualitative PCR where the sample tube contains the test sample and a plurality of different fluorescent dyes, it is of advantage to correspondingly use a plurality of excitation light sources which are disposed around each sample well and can be alternately switched on, i.e. only one at any time. In this case the excitation light beam from each of the plurality of excitation light sources has a specific wavelength or wavelength spectrum adapted to excite only one from the plurality of different fluorescent dyes. It is preferable to use a plurality of differently colored LEDs which are matched to the different fluorescent dyes. The excitation light beam from each of the excitation light sources can be passed through an optical excitation filter which is matched or specific to the particular excitation light source in order to transmit a single wavelength which contributes to the excitation of one of the different dyes and to block any other unwanted wavelengths eventually emitted by the excitation light source.

In the device for performing Real-Time/Qualitative PCR any fluorescence emitted by the fluorescent dyes in the sample is preferably detected by a single photodiode that is positioned directly underneath the sample tube. Furthermore an optical emission filter is located between the bottom end of the sample tube and the detector surface of the fluorescence detector. In order to be able to perform Multiplex Real-Time/Qualitative PCR, enabling detection and/or quantification of multiple DNA target genes in a single multiplex reaction, the emission filter is preferably a multi narrow band-pass filter which is designed to transmit only the wavelengths particular to the fluorescence emission spectra associated with the all the dyes in the sample tubes, whereas it blocks all other wavelengths.

In this case excitation filters between the excitation light sources and the side wall of the associated sample tube may be dispensable if the excitation light sources are LEDs with a narrow band spectral output light beam and if a multiple narrow band-pass emission filter is disposed between the bottom end of each sample tube and associated photodiode.

The device according to the invention comprises a plurality of sample wells in order to speed up fluorescence measurement of a given number of samples. For example the number of sample wells may be 2, 6, 10 or 12 or any other suitable number. In order to eliminate crosstalk between neighboring wells it is preferable to energize the excitation light sources of neighboring wells alternately or cyclically by first switching on the excitation light sources of the odd numbered wells and then the excitation light sources of the even numbered wells after the excitation light sources of the odd numbered wells have been switched off again, etc.

In order to be able to rapidly raise and lower the temperature of the test samples within the sample tubes the sample wells for receiving the sample tubes are preferably openings or cavities in a thermally conductive block which in turn is in intimate contact with a Peltier device for both heating and cooling the test sample. Alternative material types for the thermally conductive block include metals like aluminum and silver and thermally conductive plastics or resins, e.g. CoolPoly D-Series, i.e. thermally conductive mouldable polymers which are available from Cool Polymers, Inc., North Kingstown, R.I., USA, all of which are chosen to enhance heat transfer.

In the device for performing Melting Curve Analysis which needs only one excitation light source for each sample well the Peltier device preferably has an upright orientation and is advantageously mounted to the thermally conductive block on the side opposite from the excitation light source. In the device for performing Real-Time/Qualitative PCR the thermally conductive block with the openings or cavities for receiving the sample tubes preferably comprises at its bottom end a unitary plate like extension in intimate contact with the Peltier device.

The present invention is illustrated by reference to the drawing figures, encompassing different views of two preferred embodiments of the invention, wherein.

The optical configuration 10 and the optical-type thermal cycler 12 as depicted in FIGS. 1 to 4 of the drawing are for use in Melting Curve Analysis, i.e. a measurement of the dissociation-characteristics of test samples 14 of double-stranded DNA against temperature during heating.

Figure 1:
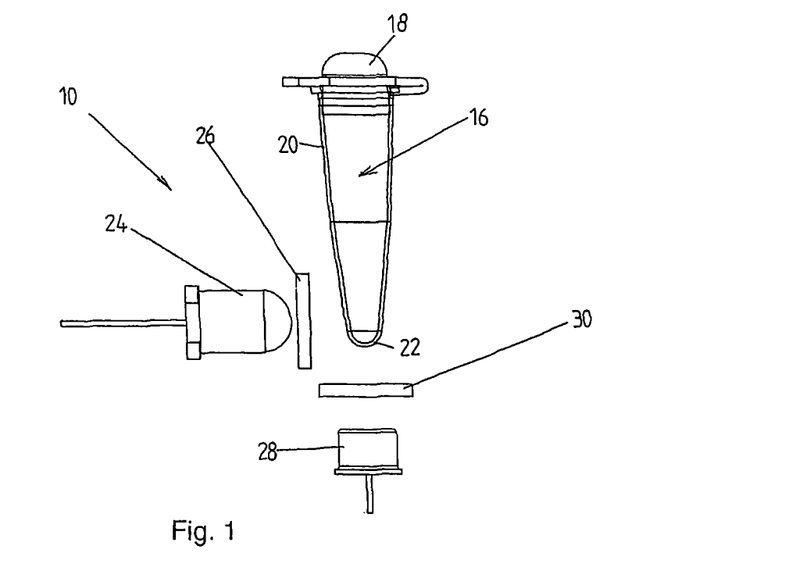
FIG. 1 is a schematic view of an optical configuration of an optical-type thermal cycler according to the invention for performing Melting Curve Analysis.
Figure 2:
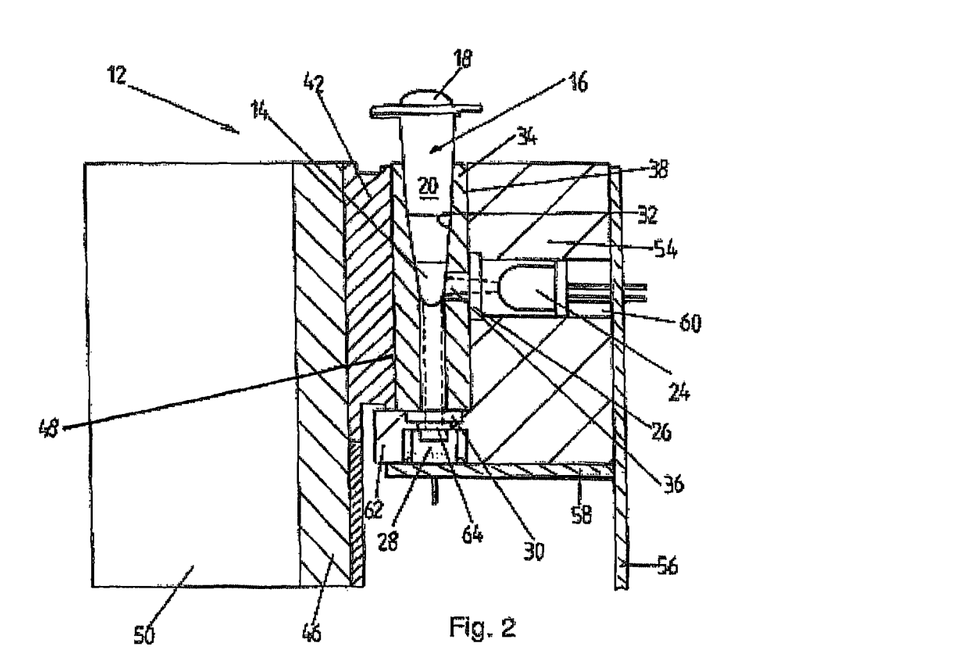
FIG. 2 is a part sectional view of the thermal cycler incorporating the optical configuration according to FIG. 1.

Each test sample 14 is contained in a standard micro-centrifuge tube 16, as best shown in FIGS. 1 and 2. The micro-centrifuge tubes 16 are consumables made from transparent polyethylene which has a light transmittance of less than 85%, i.e. the micro-centrifuge tubes 16 are not made of an optical grade plastic material. The top of each micro-centrifuge tube 16 is provided with a hinged lid 18 which is kept closed during the measurement in order to prevent contamination. The micro-centrifuge tubes 16 have a side wall 20 comprising a slightly conical upper portion and a somewhat more pronounced conical lower portion for containing the test sample 14 and further have a rounded bottom wall or end 22.

To the DNA test samples 14 in the micro-centrifuge tubes 16 is added a single fluorescent dye, like Sybr Green, that intercalates or binds only with double-stranded DNA (ds-DNA) so that a decrease in the amount of double-stranded DNA during dissociation of the DNA results in a corresponding decrease in fluorescence intensity during the excitation of the dye with a suitable excitation wavelength.

In order to measure the fluorescence intensity of the dye in one of the test samples 14 the excitation light beam from a single LED 24 is directed through an optical excitation filter 26 and through the transparent side wall 20 of the micro-centrifuge tube 16 containing the test sample 14. The LED 24 is adapted to emit a wavelength spectrum comprising a wavelength for exciting the fluorescent dye added to the test sample 14. The excitation filter 26 is adapted to block any wavelengths in the wavelength spectrum of the LED 24 which do not contribute to the excitation of the fluorescent dye. For the detection of the fluorescence of the dye which results from the excitation and exits through the transparent bottom end 22 of the micro-centrifuge tube 16 a single photodiode 28 is positioned underneath the bottom end 22 of the micro-centrifuge tube 16. A single narrow band-pass emission filter 30 in the light path between the bottom end 22 of the micro-centrifuge tube 16 and the photodiode 28 is adapted to transmit only the fluorescence emission spectrum associated with the dye, i.e. the resultant fluorescence upon excitation with the LED 24, and to block any other wavelength.

Figure 3:
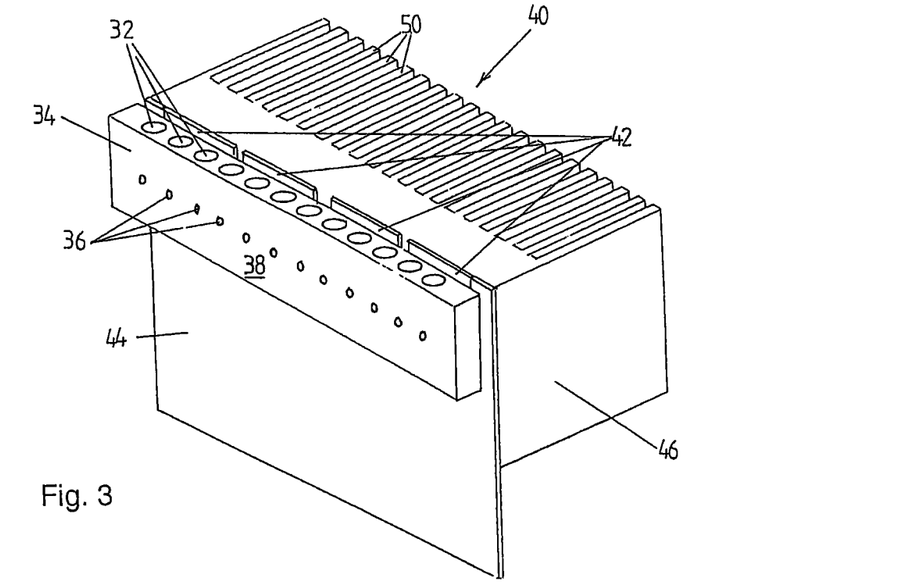
FIG. 3 is a perspective view of an assembly of parts incorporated in the thermal cycler according to FIG. 2.
Figure 4:
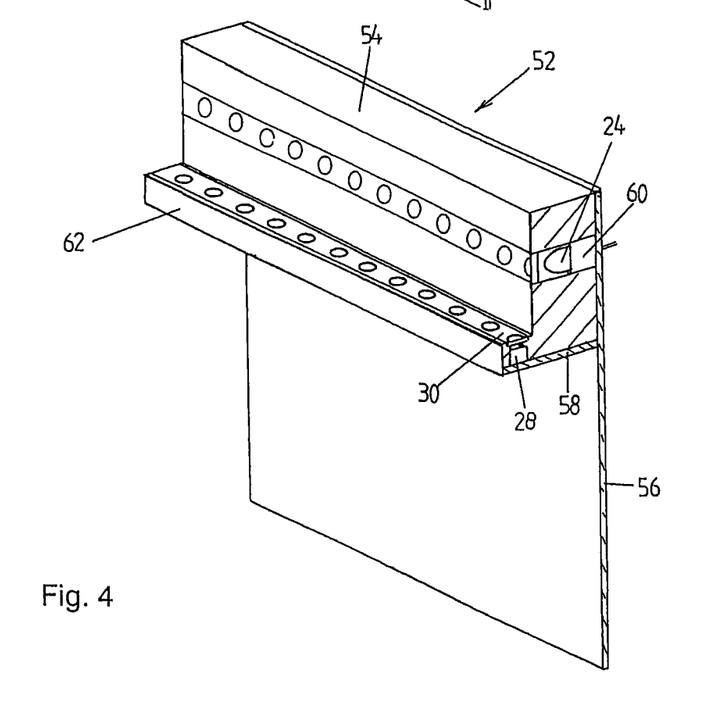
FIG. 4 is partially cut off perspective view of another assembly of parts incorporated in the thermal cycler according to FIG. 2.

In order to conduct the Melting Curve Analysis simultaneously in a number of test samples 14 the optical type thermal cycler 12 in FIGS. 2 to 4 comprises a number of sample wells 32 and a corresponding number of LEDs 24 and photodiodes 28 each one associated with one of the sample wells 32.

As can be best seen in FIGS. 2 and 3 the vertical sample wells 32 are parallel through holes in an elongated rectangular thermally conductive block 34. As can be seen in FIG. 2 each of the through holes comprises a cylindrical lower portion and an upwardly enlarged upper portion. The dimensions of the upper portion are adapted to the dimensions of the micro-centrifuge tubes 16 so that the latter ones fit snugly into the sample wells 32 with their upper end projecting from the sample wells 32. The thermally conductive block 34 can be made of a metal, like aluminum or silver, or of a thermally conductive polymer material and comprises a corresponding number of horizontal boreholes 36 which are perpendicular to the through holes. As can be seen in FIG. 2, each borehole extends from one side face 38 of the thermally conductive block 34 into one of the sample wells 32.

The thermally conductive block 34 is part of a thermal assembly 40 depicted in FIG. 3 which further comprises four Peltier devices 42, a printed circuit board 44 and an aluminum heat sink 46 with a plurality of cooling fins 50. The Peltier devices 42 are used to rapidly heat or cool the test samples 14 in the micro-centrifuge tubes 16 inserted into the sample wells 32, depending on the mode of operation of the thermal cycler 12. As can be best seen in FIG. 2 the Peltier devices 42 are mounted in intimate contact to a side face 48 of the thermally conductive block 34 which is opposite from the side face 38. The thermal cycler 12 further comprises a fan (not shown in the drawings) for blowing air across the fins 50 of the heat sink 46.

The LEDs 24 and the photodiodes 32 are part of an optical assembly 52 depicted in FIG. 4 which further comprises an optics block 54 housing the LEDs 24 and the photodiodes 32, the excitation filter 26, the emission filter 30, and two printed circuit boards 56, 58. The optics block 54 has a number of parallel horizontal bores 60 one for each of the LEDs 24. On one side the optics block 54 is provided with a projecting ledge 62 having a number of parallel vertical bores 64. Each bore 64 houses one of the photodiodes 28 with its detector surface oriented upwardly. The bores 60 and 64 have the same spacing and are associated to each other. The side of the optics block 54 which is located above the projecting ledge 62 and the upper side of the projecting ledge 62 are each provided with an elongated shallow rectangular cavity for holding the excitation filter 26 and the emission filter 30 respectively which are each in the shape of an elongated rectangular slab fitted into the corresponding cavity.

After the mounting of the assemblies 40 and 52 in the thermal cycler 12 as shown in FIG. 2 the ledge 62 projects beneath the metal block 34 such that the side face 38 of the metal block 34 abuts to the side of the optics block 54 and the bottom surface of the metal block 34 abuts to the upper side of the ledge 62 and the vertical bores 64 in the ledge 62 are in alignment with the through holes of the sample wells 32 and the bores 36 of the thermally conductive block 34 are in alignment with the bores 60 of the optics block 54.

In addition the thermal cycler 12 is provided with a lid (not shown in the drawings) which is movable between an open position for introducing the micro-centrifuge tubes 16 into the sample wells 32 and a closed position for covering the upper ends of the micro-centrifuge tubes 16 projecting from the sample wells 32. In the closed position the lid applies a pressure to the caps 18 of the tubes 16 in order to keep the caps 18 closed and the tubes 16 in good thermal contact with the thermally conductive block 34 during thermal cycling. The lid is provided with a resistance heater which heats the air in the top of the closed tubes 16 for minimizing sample evaporation and preventing the samples 14 from condensing in the top of the tubes 16.

In a number of tests which were conducted with the optical configuration 10 according to FIG. 1 in the thermal cycler 12 according to FIGS. 2 to 5 surprisingly it was found that notwithstanding the use of standard micro-centrifuge tubes 16 made of transparent polyethylene a very good correlation between the temperature of the test samples 14 and the fluorescence intensity measured by the photodiodes 28 could be achieved so that there was no need to manufacture the micro-centrifuge tubes 16 from a more expensive optical grade plastic material having a light transmittance of more than 90%.

Figure 5:
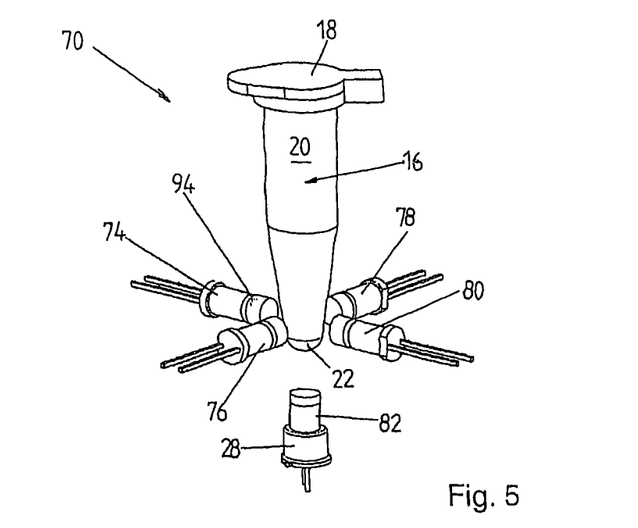
FIG. 5 is a schematic view of an optical configuration of another optical-type thermal cycler according to the invention for performing Real-Time/Qualitative PCR.
Figure 6:
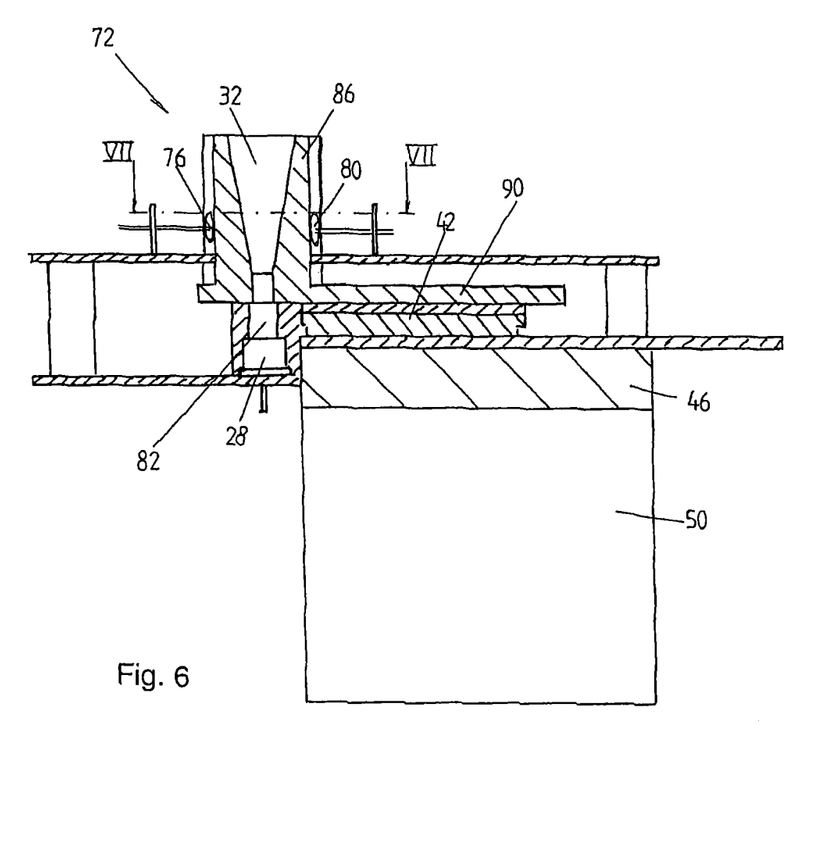
FIG. 6 is a part sectional view of the thermal cycler incorporating the optical configuration according to FIG. 5.
Figure 7:
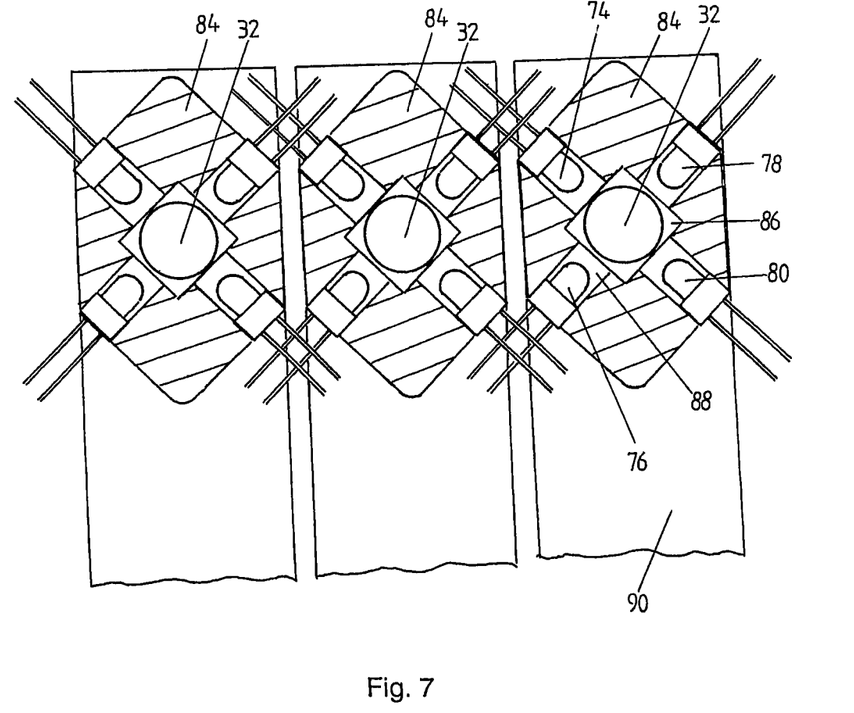
FIG. 7 is a cross sectional view taken along line VII-VII in FIG. 6.

The optical configuration 70 and the optical-type thermal cycler 72 as depicted in FIGS. 5 to 7 of the drawing are for use in Real Time/Qualitative PCR, i.e. the simultaneous detection and quantification of multiple target genes in an amplified DNA sequence in DNA test samples 14 by means of optical fluorescence measurement in a single multiplex reaction. Each test sample 14 is again contained in a standard micro-centrifuge tube 16, as best shown in FIG. 5, together with four different fluorescent dyes, which intercalate or bind only with double-stranded DNA (dsDNA). An increase in the amplified DNA sequence during PCR leads to an increase in fluorescence intensity emitted by the dyes upon excitation with suitable wavelength spectra. By measuring the fluorescence intensity DNA concentrations can be quantified by comparison with a standard sample dilution.

For conducting the Real Time/Qualitative PCR simultaneously in a number of test samples 14 the thermal cycler 72 according to FIGS. 6 and 7 also comprises a number of sample wells 32 with a photodiode 28 beneath the bottom end of each sample well 32. However in contrast to the optical thermal cycler 12 as described before, in the optical thermal cycler 72 instead of one LED there are four differently colored LEDs 74, 76, 78, 80 associated with each sample well 32 and a quadruple narrow band-pass emission filter 82 instead of the single emission filter 64.

In order to measure the fluorescence of the four dyes in each of the test samples 14 the excitation light beams from the four LEDs 74, 76, 78, 80 of each sample well 32 are simultaneously directed through the transparent side wall 20 of the micro-centrifuge tube 16 containing the test sample 14. The four LEDs are adapted to emit different wavelength spectra each comprising a wavelength for exciting one of the fluorescent dyes added to the test sample 14. Each of the LEDs 74, 76, 78, 80 can be provided with a corresponding excitation filter 94, as shown in FIG. 5. However the excitation filter 94 can also be dispensed with, as shown in FIG. 7. The intensity of the resultant fluorescence of the dyes exiting through the transparent bottom end 22 of the micro-centrifuge tube 16 is again detected by the single photodiode 28 beneath the sample well 32 and the quadruple narrow band-pass emission filter 82. This latter filter 82 in the light path between the bottom end 22 of the micro-centrifuge tube 16 and the photodiode 28 is adapted to transmit only the fluorescence emission spectra associated with the four dyes and to block any other wavelength.

As can be seen from FIG. 7, the vertical sample wells 32 are cavities having the profile of a micro-centrifuge tube 16. Each well 32 is provided in a single thermally conductive block 86. Each block 86 is inserted into a correspondingly shaped through-hole of an optics block 84, the optics block 84 having a generally hexagonal cross-section.

The optics block 84 is provided with four horizontal through bores 88 aligned with corresponding bores (not visible) in the thermally conductive block 86 and opening into the sample well 32 each one for housing one of the LEDs 74, 76, 78, 80. The through bores 88 and the LEDs 74, 76, 78, 80 are equally spaced in the circumferential direction of the micro-centrifuge tube 16 in the sample well 32.

For heating and cooling the test sample 14 contained within the micro-centrifuge tube 16 in the sample well 32 each thermally conductive block 86 features a plate-like horizontal extension 90 which extends in parallel to a Peltier device 42 mounted beneath the plate-like extension 90. The upper surface of the Peltier device 42 is in intimate contact with the plate-like extension of 90 of the thermally conductive block 86. A heat sink 46 made of aluminum with a plurality of fins 50 is mounted underneath the Peltier device 42.

In contrast to the thermal cycler 12 in FIGS. 1 to 4 the thermal cycler 72 according to FIGS. 5 to 7 does not have a heated lid. Instead an oil or wax overlay is added on top of the samples 14 in the sample tubes 16 for preventing evaporation. In this way the lids 18 of the sample tubes 16 may be left open during thermal cycling in order to avoid any problems associated with the automatic closure of the lids 18.

When using the thermal cycler 72 the LEDs 74, 76, 78, 80 in each optics block 84 are alternately switched on, i.e. one at any time. In order to eliminate crosstalk between neighboring sample wells 32 in the optical thermal cycler 72 the LEDs 74, 76, 78, 80 of neighboring sample wells 32 are switched on and off alternately or cyclically. In other words the LEDs 74, 76, 78, 80 of all the odd numbered sample wells 32 in the row of sample wells 32 as partially shown in FIG. 7 are successively switched on while the LEDs 74, 76, 78, 80 of all the even numbered sample wells 32 are off, and then the LEDs 74, 76, 78, 80 of all the even numbered sample wells 32 are successively switched on while the LEDs 74, 76, 78, 80 of all the odd numbered sample wells 32 are off.

When performing Real Time/Qualitative PCR with FRET-type fluorophore-containing DNA probes, such as TaqMan, in the thermal cycler 72 of FIGS. 5 to 7 it is possible to use only one of the LEDs 74, 76, 78, 80 in combination with the quadruple narrow band-pass emission filter 82.

In a number of tests which were conducted with the optical configuration 70 according to FIG. 5 in the thermal cycler 72 according to FIGS. 6 and 7 it was also found that notwithstanding the use of standard micro-centrifuge tubes 16 made of transparent polyethylene a very good correlation between the quantity of the multiple target genes in the test samples 14 and the fluorescence intensity measured by the photodiodes 28 could be achieved so that there was no need to manufacture the micro-centrifuge tubes 16 from a more expensive optical grade plastic material with a light transmittance of more than 90%.

The invention claimed is:
1. A thermal cycler device for optically measuring fluorescence of test samples comprising:
   a plurality of upright sample tubes made of a transparent material, having a side wall, a bottom end and containing one of the test samples,
   a plurality of vertical sample wells each for receiving one of the upright sample tubes,
   at least one excitation light source for directing an excitation light beam through the side wall of a sample tube into the test sample, and
   an optical fluorescence detector for capturing fluorescence emitted from the test sample upon excitation,
wherein
   the test samples contain nucleic acids and a plurality of fluorescent dyes,
   the device comprises a plurality of excitation light sources disposed around each sample well, each excitation light source being disposed in the vicinity of the associated sample well for exciting the dye in a test sample in the sample well;

the device comprises a plurality of optical fluorescence detectors, which are disposed underneath the bottom end of each sample tube which captures fluorescence emitted from the dye in the test sample upon excitation, the axis of the sample tube received in the sample well is in alignment with the fluorescence detector, characterized in that the sample wells are each provided in a single thermally conductive block, each thermally conductive block is inserted into a through-hole of an optics block, the optics block is provided with at least four horizontal through bores disposed around each sample well, each through bore houses one of the plurality of excitation light sources that are disposed around each sample well, wherein the plurality of excitation light sources comprises four LED excitation light sources, and wherein each of the four LED excitation light sources has a different wavelength spectrum for exciting one of the plurality of fluorescent dyes, and each through bore is aligned with a corresponding bore of the thermally conductive block that opens into the sample well.

2. The thermal cycler device according to claim 1, wherein the sample tubes are micro-centrifuge tubes made of a plastic material with a light transmittance of less than 90%.

3. The thermal cycler device according to claim 1, wherein the excitation light sources are LEDs.

4. The thermal cycler device according to claim 1, wherein the optical fluorescence detectors each comprise a single photodiode.

5. The thermal cycler device according to claim 1, wherein an excitation filter is disposed in a path of the excitation light beam between the excitation light sources and the side walls of the sample tubes, the excitation filter being adapted to transmit only light of a specific wavelength.

6. The thermal cycler device according to claim 1, wherein a narrow band-pass emission filter is disposed between the bottom ends of the sample tubes and the optical fluorescence detectors, the emission filter being adapted to transmit only the fluorescent light emitted from at least one dye.

7. The thermal cycler device according to claim 1, further comprising a lid which is movable between an open position for introducing the sample tubes into the sample wells and a closed position for covering the plurality of sample wells, and a resistance heater in the lid.

8. The thermal cycler device according to claim 1, further comprising an overlay in each sample tube for covering the test sample in the sample tube.

9. The thermal cycler device according to claim 1, wherein a multiple narrow band-pass emission filter is disposed between the bottom ends of the sample tubes and the optical fluorescence detectors and wherein the emission filter is adapted to transmit only the fluorescent light emitted from the plurality of fluorescent dyes.

10. The thermal cycler device according to claim 1, adapted for alternately energizing the excitation light sources of neighboring sample wells.

11. The thermal cycler device according to claim 1, further comprising at least one Peltier device for heating and cooling the test samples in the sample wells, the Peltier device being in intimate contact with a thermally conductive block surrounding the sample wells.

12. The thermal cycler device according to claim 1, wherein the cross sectional shape of the sample wells for receiving the upright sample tubes is adapted to the cross sectional shape of the sample tubes.

13. A process for utilizing the thermal cycler device according to claim 1 for Real Time/Qualitative PCR comprising detecting and quantifying multiple target genes in an amplified DNA sequence in DNA test samples by measuring optical fluorescence.

* * * * *